United States Patent
Kaspar

(10) Patent No.: US 10,588,767 B2
(45) Date of Patent: Mar. 17, 2020

(54) STENT COMPRISING A RETAINING ELEMENT

(71) Applicant: Bentley InnoMed GmbH, Hechingen (DE)

(72) Inventor: Klaus Kaspar, Graz (AT)

(73) Assignee: Bentley InnoMed GmbH, Hechingen (DE)

( * ) Notice: Subject to any disclaimer, the term of this patent is extended or adjusted under 35 U.S.C. 154(b) by 0 days.

(21) Appl. No.: 15/033,794

(22) PCT Filed: Nov. 4, 2014

(86) PCT No.: PCT/EP2014/073635
§ 371 (c)(1),
(2) Date: May 2, 2016

(87) PCT Pub. No.: WO2015/063312
PCT Pub. Date: May 7, 2015

(65) Prior Publication Data
US 2016/0250052 A1    Sep. 1, 2016

(30) Foreign Application Priority Data
Nov. 4, 2013    (DE) .................... 10 2013 018 426

(51) Int. Cl.
*A61F 2/95*      (2013.01)
*A61F 2/954*     (2013.01)
*A61F 2/90*      (2013.01)
*A61F 2/856*     (2013.01)
*A61F 2/82*      (2013.01)
*A61F 2/958*     (2013.01)

(52) U.S. Cl.
CPC .............. *A61F 2/954* (2013.01); *A61F 2/856* (2013.01); *A61F 2/90* (2013.01); *A61F 2/958* (2013.01); *A61F 2002/821* (2013.01); *A61F 2230/0069* (2013.01)

(58) Field of Classification Search
CPC .. A61F 9/90; A61F 9/954; A61F 9/856; A61F 9/958; A61F 2230/0069; A61F 2002/821; A61F 2002/9511
USPC ..................................... 623/1.11
See application file for complete search history.

(56) References Cited

U.S. PATENT DOCUMENTS

| | | | |
|---|---|---|---|
| 2007/0043381 A1* | 2/2007 | Furst ...................... | A61F 2/962 606/108 |
| 2008/0262592 A1* | 10/2008 | Jordan ..................... | A61F 2/95 623/1.11 |
| 2010/0324651 A1* | 12/2010 | Holzer ..................... | A61F 2/90 623/1.15 |
| 2011/0125252 A1* | 5/2011 | Goddard ................... | A61F 2/95 623/1.23 |

(Continued)

FOREIGN PATENT DOCUMENTS

| EP | 1870057 A1 | 12/2007 |
|---|---|---|
| WO | 2007104051 A2 | 9/2007 |

*Primary Examiner* — Erich G Herbermann
(74) *Attorney, Agent, or Firm* — Brooks Kushman P.C.

(57) ABSTRACT

The invention relates to a stent (12) to be positioned in the bifurcation/branching (14) of a blood vessel (16), wherein the stent (12) is composed of a plurality of meshes (10) and has a distal (18) and a proximal end (20), characterized in that the stent is provided with a retaining element (22) that passes through oppositely arranged meshes (10) at the proximal end (20) of the stent (12).

6 Claims, 3 Drawing Sheets

(56) References Cited

U.S. PATENT DOCUMENTS

2012/0172965 A1* 7/2012 Kratzberg ............... A61F 2/962
                                                    623/1.12
2013/0006347 A1* 1/2013 McHugo ................... A61F 2/95
                                                    623/1.12

* cited by examiner

STENT COMPRISING A RETAINING ELEMENT

The invention relates to stent to be positioned in the bifurcation/branching of a blood vessel, wherein the stent is composed of a plurality of meshes and has a proximal end and a distal end.

According to prior art various insertion systems are known for stents, for example braided stents or balloon expandable stents, to be placed in a predetermined position in the bifurcation or branching of a blood vessel. However, positioning the stent with customary methods has proved problematic; complications have even been encountered in simple T-branches and V-bifurcations when placing the stents in position. Such complications have especially been experienced when the respective slant end projects into the main vessel from which the bifurcation branches off. In such a case blood clots may form that could lead to vascular obiterations. Moreover, when the ends of a stent that is positioned in the bifurcation project into the main vessel this also makes start navigation in the main vessel more difficult. Complications have in particular been encountered with branches in the form of V-bifurcations having angles less than 70° between the two arms or branches.

In the light of the above, there is need for the improvement of insertion systems for stents to be positioned in vessel branching locations with a view to enhancing the stent positioning accuracy at the placement site.

According to the invention, this objective is achieved by providing a stent of the kind first mentioned above, wherein a retaining element is arranged that passes through the oppositely arranged meshes at the proximal end of the stent.

Preferred embodiments of the invention are described in the respective sub-claims that either individually or in combination may constitute and outline an aspect of the invention.

As proposed by the present invention the stent to be placed in the vascular branch or bifurcation is of customary design having a proximal and a distal end as well as a plurality of meshes or cells, wherein the retaining element passes through oppositely arranged meshes at the proximal end of the slant. Expediently, the retaining element is connected to a guidewire, in a preferred embodiment to the distal end of the guidewire, with said element being drawn from the outside through oppositely arranged meshes of the stent at the stent's proximal end. The retaining element can be removed and will be taken out of the blood is vessel and the stent after stent placement has been completed. In particular, the retaining element consists of wire but may also be made of a plastic material that offers adequate stiffness. Preferred materials for the retaining element are medical steel and Nitinol.

It shall be understood that the term proximal as it used here refers to the end of the guidewire or stent facing the attending physician whereas the term distal denotes the end that is situated away from the attending physician.

The term stent denotes a medical implant introduced into a vessel with a view to widening or expanding said vessel or keeping it open. For example, a lattice structure of tubular form made of metal or plastic may be employed for said stent, wherein the stent may be cut to size from a suitable tube, for instance by a laser cutting method, or may be of braided design. Materials for stent are of customary nature, with shape-memory materials for example Nitinol or spring steel being used for self-expanding slants while medical steel suitable for the purpose being selected as material for balloon-expandable stents.

The term meshes or cells refers to the apertures or openings that exist in the lattice structure of the stent. Oppositely arranged meshes or cells are apertures existing on the periphery of the stent and facing one another on opposite sides.

During placement, the stent with its retaining element according to the invention navigated to the placement site by means of a catheter in a manner known per se, usually crimped onto a balloon by means of which the expansion is brought about later. The retaining element is preassembled and transferred to the placement site together with the stent by means of the catheter. In the event the retaining element consists of a single wire, for example the end of the to guidewire, said element is arranged in the catheter in double-angled form, with the angled end pointing in proximal direction. Having been liberated from the catheter, that is after the stent has arrived at the intended placement site, the retaining element folds out exactly in front of the branching off vessel in such a way that the stent with its proximal end is precisely arranged at the point where is the vessel branch actually star. After expansion has been brought about by means of a balloon or by self-expansion the retaining element, in this case in the form of the guidewire, is drawn back and the stent has now reached its final and precisely predetermined position.

As per another preferred embodiment of the invention the retaining element has a T-form with two arms in its distal region, said arms extending from the inside through oppositely arranged meshes of the stent. In this case, the horizontal bar of the T-form constitutes the retaining element, wherein the vertical bar of the T being attached to the guidewire thus terminating at the proximal end of the stent and at most projecting only slightly into the inside of the stent.

In this embodiment as well the free ends of the retaining element projecting from the stent are angled in proximal direction and in this configuration are moved by a catheter. When the catheter is retracted after the stent has reached its intended position the free ends spread or fold out, are placed in position in front of the branching-off vessel, and in this manner secure the stent at the place where it will expand or be expanded.

Expediently, retractable tube by means of which the stent is navigated together with its retracting element and pertinent guidewire and as the case may be with the respective expansion device may also perform the catheter function. Said tube is retractable and will be removed immediately after the stent has been placed in position thus allowing the free ends of the retaining element to fold out.

To make sure the retaining element has the desired degree of flexibility it is advantageously made of spring steel or a nickel-titanium alloy having shape-memory properties (Nitinol).

It is to be understood and the invention provides for the stent and retaining element to form an integral unit and be available in preassembled state. The same applies to a kit comprising a stent crimped onto a balloon, a retaining element with guidewire, where appropriate the retractable tube, as well as the placement catheter.

It shall furthermore be understood that any stent may be employed as stent that has the respective apertures in the form of a cell or mesh structure. Accordingly, any customary stent featuring this structure may be modified within the meaning of the invention and be provided with said retaining element. This enables a wide range of stents to be used that can be implanted in a vessel branch and meet the requirements called for by the respective vessel structure. What always remains the same is the principle of a "locking bar" arranged at the vessel branch in the form of the free end or ends of the retaining element which enables the stent to be placed as precisely as possible.

It shall, moreover, be understood that the stent can be adapted to the relevant form of the branch, and, particularly at the proximal end, may be of oblique configuration.

Further elucidation of the invention is provided by way of examples through the following figures with the detailed features representing an aspect of the invention both individually and in any discretionary combination, where FIG. 1 is a schematic view of an insertion system with an inventive stent introduced in a vessel according to a first embodiment;

Figure 1:
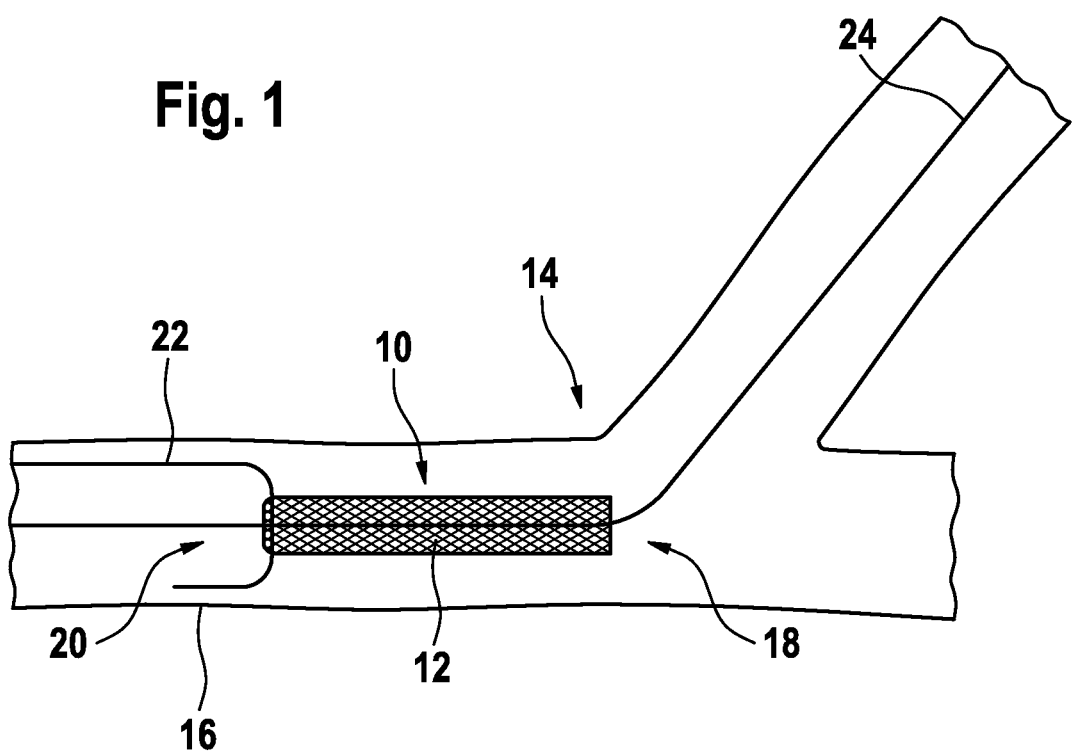

FIG. 1 illustrates the system for the positioning of a stent 12 in the bifurcation 14 of a blood vessel in the present case a V-branch. Stent 12 comprises a plurality of meshes 10 at the distal end 18 and at proximal end 20. To keep the stent in a predetermined position in branch 14 of the vessel 13 a retaining element 22 is passed from the outside through oppositely arranged meshes 10 at the proximal end 20 of the stent, in this case the distal end 22 of a conventional guidewire. For attachment to stent 12 the distal end 22 of the guidewire is run from the outside through two meshes 10 located opposite to each other at the proximal end 20 of the stent 12 in such a manner that the free end of the guidewire protrudes at the sides of the stent. During navigation, the guidewire and the end assume an angulated position, especially when transported in a conventional catheter, and after the stent has been released from the catheter the distal end 22 of the guidewire folds out and is kept in position in front of branch 14 of the vessel 16.

The stent, as rule, is of balloon-expandable type that with the help of the balloon expands hydraulically after placement thus bringing the stent in secure contact with the vessel walls. After attachment to the wall of the vessel the retaining element 22 is no longer needed and can be extracted and removed from its position at the proximal end 20 of the stent 12. The balloon-induced expansion of the stent is brought about by adopting customary methods and customary means.

Not shown in FIG. 1 is that the retaining element 22 and at least the proximal end 20 of stent 1 pray be arranged in a tube that can be retracted with a view to releasing the stent and the retaining element.

As can be seen from FIG. 1, the stent 12 that is crimped onto a customary balloon (not shown) is pushed forward with the aid of a common guidewire until it is has reached its predetermined position in the branch 14 of the vessel 16. The illustration shows the guidewire 24 used for the placement of the stent. Moreover, the retaining element 22 is passed through the stent 12 in such a manner that the end portion protrudes from the stent. While the stent 12 is in the process of being inserted, the retaining element 22 is enclosed in the catheter basically in U-form and after the stent has reached its position and been liberated spreads out to form a locking bar, see FIG. 2.

Figure 2:
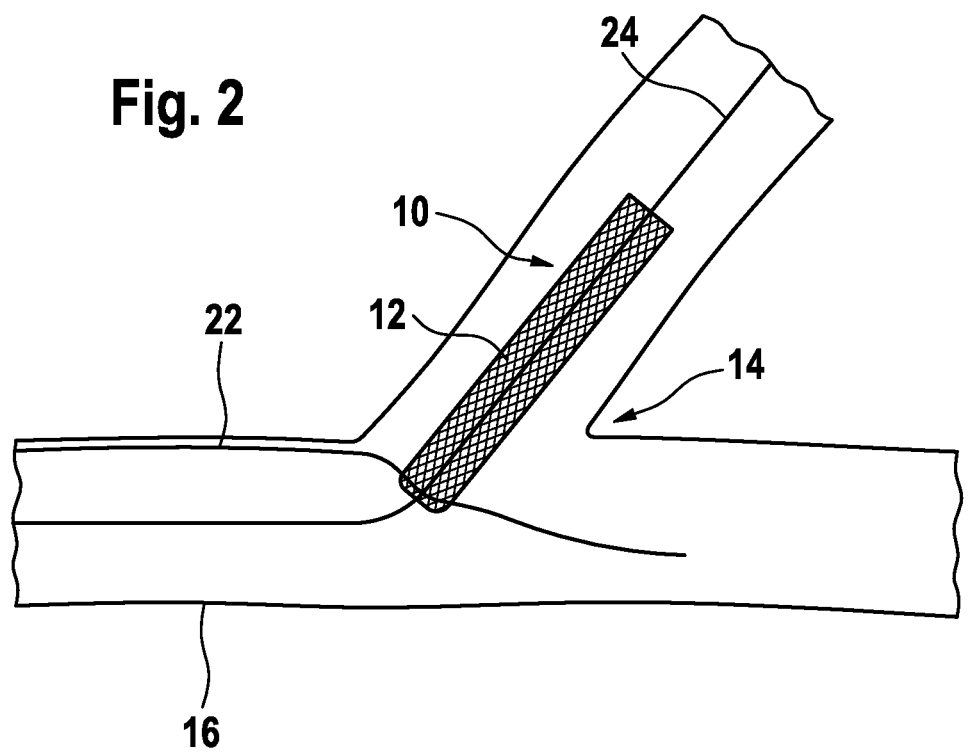
FIG. 2 is a schematic view of an insertion system in accordance with FIG. 1 with the stent being placed into a bifurcation.

FIG. 2 depicts tine nest step in tine placement of the stent 12 in branch 14 of a vascular system. The free end of the retaining element 22 spreads out and assumes a position in front of the opening of the vessel branch thus preventing the stent from being pushed further into the branch. In this predetermined position in branch 14 expansion and secure attachment takes place (by means of the balloon, not shown here).

Figure 3:
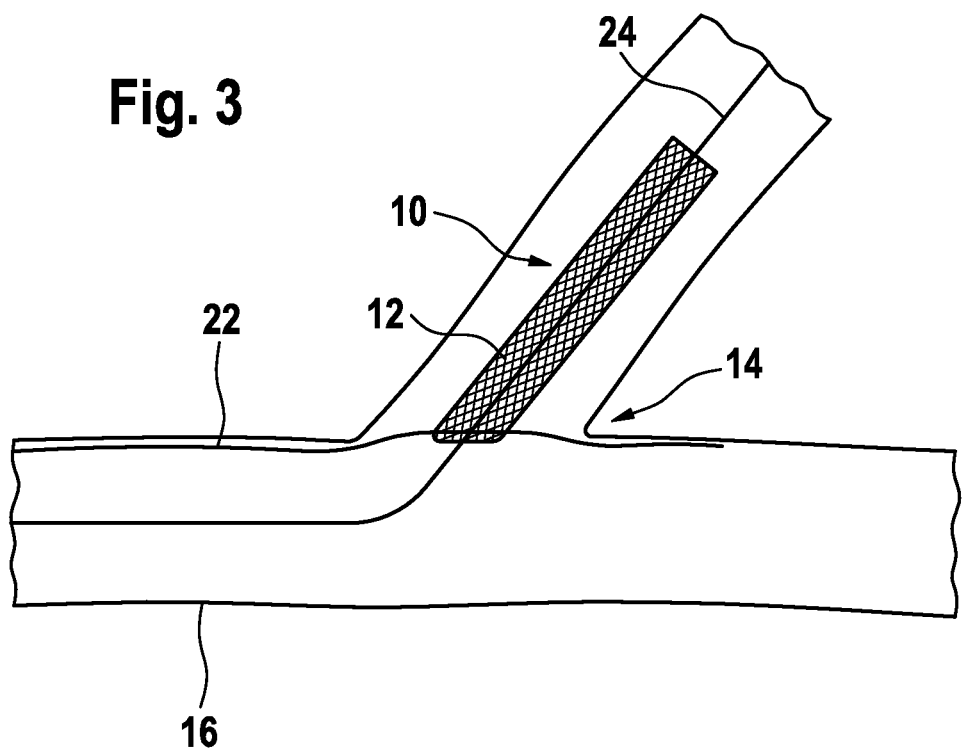
FIG. 3 is a schematic view of an insertion system in accordance with FIG. 1 after placement of the stent in the predetermined position.

FIG. 3 shows the stent 12 in its final position immediately before it is expanded. It can be easily seen that the retaining element 22 holds the stent in the desired place. Neither balloon nor catheter for the expansion have been illustrated.

In the configuration shown, the proximal stent has an oblique contour to enable the stent to adapt as best as possible the characteristics of the branching off vessel.

Figure 4:
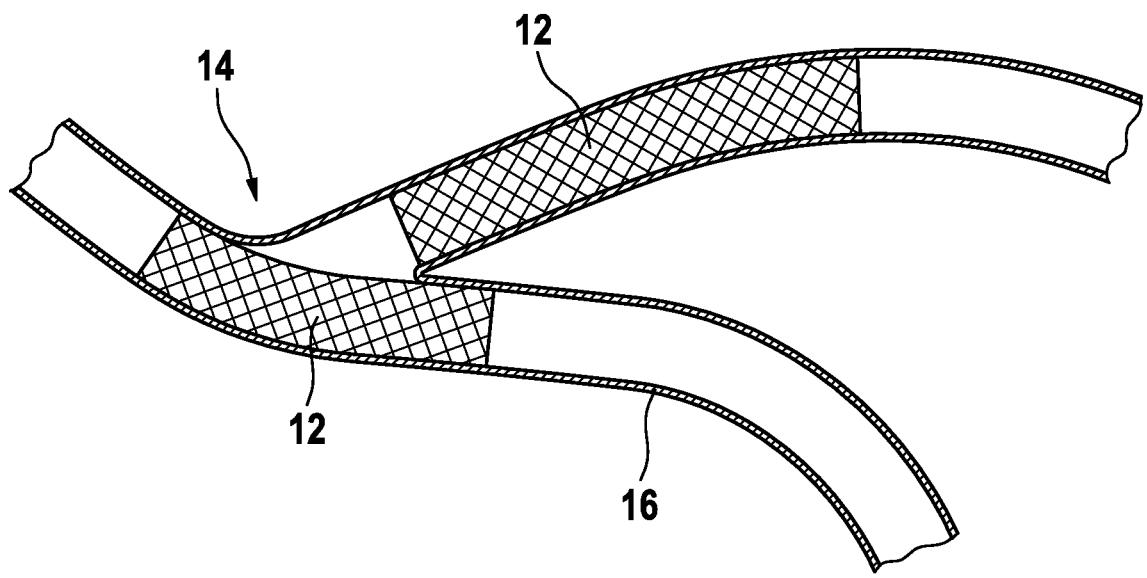
FIG. 4 illustrates a view of the stent having reached its predetermined position in the branch of a vascular model.

FIG. 4 shows a stent 1 arranged in the branch 4 of vascular system 16. After stent 12 has finally reached the intended position in branch 14 it was expanded by means of a balloon. Following this, the retaining element 22, the guidewire 24, balloon, and catheter have been removed.

It can also be seen from FIG. 4 that another stent 12 has been placed in the main vessel at a point adjacent to the branch.

Figure 5:
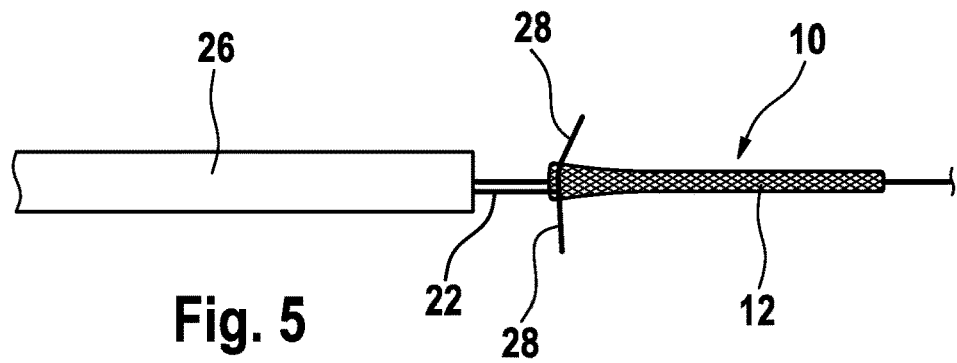
FIG. 5 is a schematic view of an insertion system with an inventive stent introduced in a vessel according to a second embodiment.

FIG. 5 shows another embodiment of the invention. In this embodiment, the retaining element 22 has been inserted in the proximal end 20 of the stent 12 with its two arms 28 protruding at the sides of the stent through two meshes. The meshes through which the two arms project are located oppositely to each other. Together with the stent and distal segment 22 of the guidewire the arms form a T. Moreover, the system is provided with a tube 26 embracing the stent 12 and the arms 28 of the retaining element 22 during navigation through the vascular system. For final placement the tube 26 is retracted; FIG. 5 shows the tube in already retracted position causing arms 28 of the retaining element 22 to be released and spread out.

Figure 6:
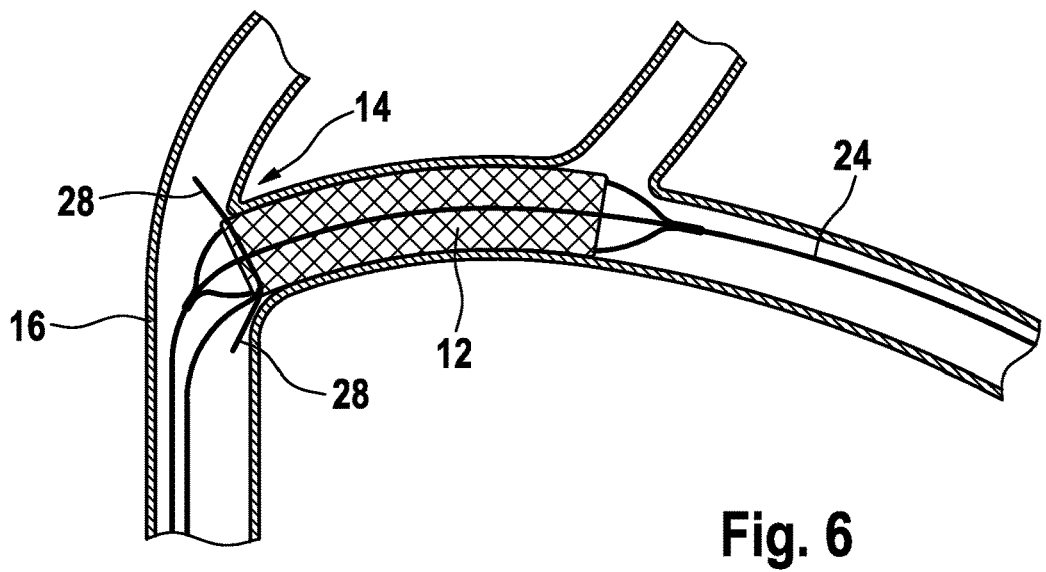
FIG. 6 illustrates the view of the insertion system according to claim 6 with the stent being positioned at its predetermined place in the bifurcation of a vascular model.
Figure 7:
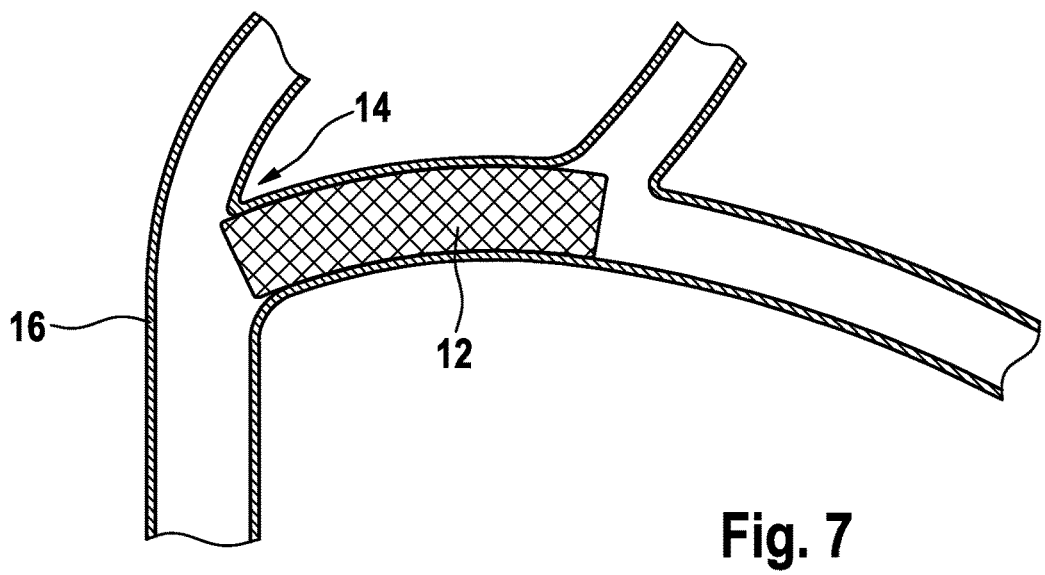
FIG. 7 is a view of the stent in its final position.

Illustrated in FIG. 6 is how the stent 12 is moved to its predetermined position in the branch 14 with the help of a guidewire 24 and how it is secured in this position by the spread-out arms 28 of the retaining element 22. After the expansion (FIG. 7) the retaining element 22, the guidewire 24, and the balloon used for expansion are retracted. The tube has already been withdrawn earlier.

It Is to be understood of course that the stents illustrated in the figures hereinbefore may also be of self-expanding type, i.e. do not need a balloon to bring about expansion.

The invention claimed is:

1. A stent to be positioned by an attending physician in a bifurcation/branching of a blood vessel, wherein the stent is composed of a plurality of meshes and has a distal end and a proximal end, wherein the stent is provided with a removable guidewire as a retaining element, the removable guidewire having one free distal end, said removable guidewire being passed from outside the stent through two oppositely arranged meshes of the plurality of meshes facing each other and situated at the proximal end of the stent such that the free distal end of the removable guidewire spreads out, protrudes from the stent and span an entire opening of the bifurcation/branching of the blood vessel to form a locking bar, thus preventing the stent from being pushed further into the bifurcation/branching of the blood vessel when the stent is fully within the bifurcation/branching of the blood vessel.

2. The stent according to claim 1, wherein the retaining element consists of a shape-memory material.

3. The stent according to claim 2, wherein the shape-memory material is Nitinol.

4. A kit comprising the stent according to claim 1 and a retractable tube, wherein the stent is enclosed within the retractable tube in such a manner that the free distal end of the retaining elements is enfolded in the retractable tube and is capable of spreading out when the retractable tube is withdrawn.

5. The stent according to claim 1, wherein the stent is balloon expandable.

6. A kit comprising a catheter and the stent according to claim 5.

* * * * *